Figure 1:
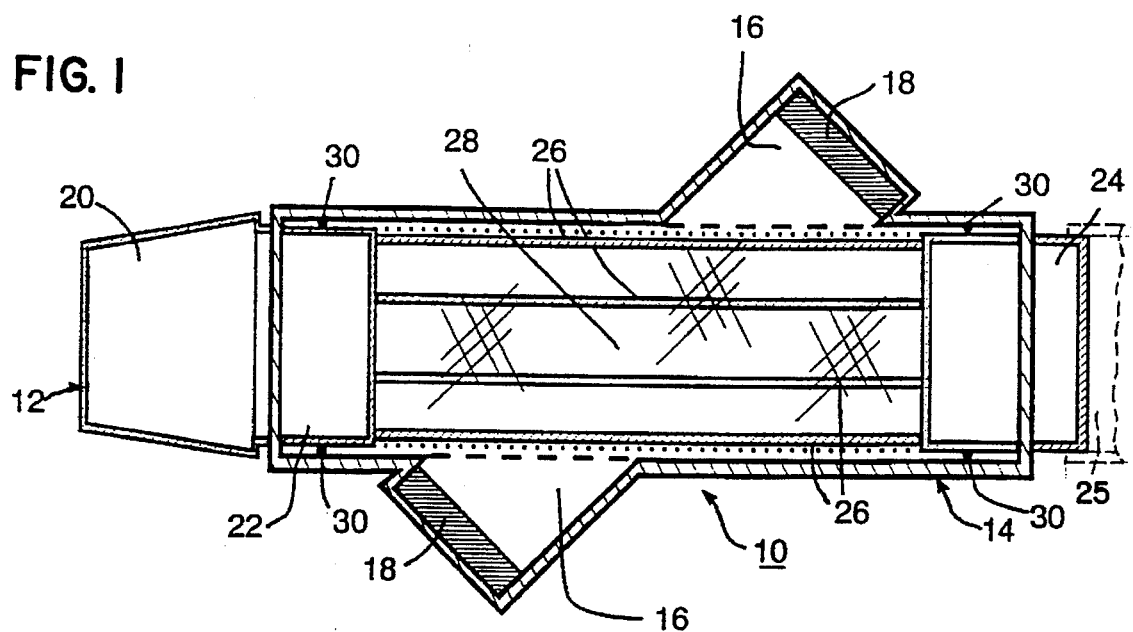

United States Patent [19]
Harnoncourt

[11] Patent Number: 5,647,370
[45] Date of Patent: Jul. 15, 1997

[54] ULTRASONIC SPIROMETER

[75] Inventor: Karl Harnoncourt, Graz, Austria

[73] Assignee: NDD Medizintechnik GmbH, Würzburg, Germany

[21] Appl. No.: 479,435

[22] Filed: Jun. 7, 1995

[30] Foreign Application Priority Data

Jul. 1, 1994 [DE] Germany .............................. 9410661 U

[51] Int. Cl.$^6$ .................................................. A61B 8/00
[52] U.S. Cl. ........................................................ 128/725
[58] Field of Search ................................... 128/716, 719, 128/725–750, 202.28, 909

[56] References Cited

FOREIGN PATENT DOCUMENTS 42 22 286 C1   5/1994   Germany .

Primary Examiner—Angela D. Sykes
Assistant Examiner—Samuel Gilbert
Attorney, Agent, or Firm—Keck, Mahin & Cate

[57] ABSTRACT

The invention relates to an ultrasonic spirometer with a graduated tube where a transmitter/receiver cell pair is positioned in a graduated portion diagonally or perpendicularly to the graduated tube axis, with an easily replaceable breathing tube being insertable into the graduated tube. The breathing tube is at least partially made from essentially one material which is permeable for ultrasonic waves, but wholly or at least largely impermeable to germs and contaminants. In accordance with the invention, the material permeable for the ultrasonic waves and wholly or at least largely impermeable to the germs and contaminants is positioned at least in the area in which the graduated portion intersects the graduated tube over the whole circumference of the breathing tube.

15 Claims, 3 Drawing Sheets

5,647,370

ULTRASONIC SPIROMETER

The invention relates to an ultrasonic spirometer.

Such an ultrasonic spirometer is already known from the German patent DE 42 22 286 C. There, to avoid cross infections, the use of an easily replaceable, largely sterile breathing tube is recommended which can be inserted into the graduated tube. At the transition to the graduated portion this breathing tube possesses graduated windows in such a form that inserts are inserted in corresponding openings which are permeable for ultrasonic waves, but largely impermeable for germs or contaminants. This solution requires that the breathing tube be inserted into the graduated tube in a certain position so that the corresponding inserts which are permeable for the ultrasonic waves and largely impermeable to the germs and contaminants lie in the area of the graduated channel. Incorrect insertion of the breathing tube leads to a lack of function.

The object of the invention is therefore to improve the generic class ultrasonic spirometer even further in that the breathing tube will be insertable into the graduated tube in any position and that the design of the breathing tube be simplified even further.

This task is solved in accordance with the invention by the characterising portion of the main claim. According to this, with a generic class ultrasonic spirometer the material being permeable for the ultrasonic waves and being largely impermeable to the germs and contaminants is, at least in that area in which the graduated portion intersects the graduated tube, positioned around the total circumference of the breathing tube. In this way, it is no longer necessary to provide single openings in which the inserts made from the corresponding material then have to be inserted. It is furthermore also no longer necessary to observe the position of the openings and the inserts with regard to the graduated channel when the breathing tube is being inserted.

Preferred embodiments are derived from the dependant claims following the main claim.

Accordingly, the breathing tube can comprise a mouthpiece, if necessary a from tube portion connected to this, a rear tube portion and a middle tube portion positioned between the mouthpiece or the front tube portion and the rear tube portion consisting of a material covering the whole circumference which is permeable for ultrasonic waves and largely impermeable to germs and contaminants.

A support element can extend between the mouthpiece or the front tube portion and the rear tube portion on which support element the material lies which is permeable for the ultrasonic waves and largely impermeable to the germs and contaminants. This support element can, for example, comprise parallel struts, but also a mesh made from plastic struts or a spiral covering the whole circumference. Thanks to the support element, the inherent stability of the material permeable for the ultrasonic waves and largely impermeable to the germs and contaminants is ensured. To avoid leaks at its corresponding joint abutments, this is lightly glued or welded, for example to the front and/or rear tube portions.

Between the front and rear tube portions of the breathing tube and the graduated tube packing washers which cover the corresponding whole circumferences can be positioned. In this embodiment, the breathing tube can be extendable on the side facing away from the patient so that it protrudes out of the graduated tube. At the rear tube portion of the breathing tube respiratory gas tubes for the feeding of certain respiratory gases can be flanged in a gas-impermeable manner using corresponding standard connections. The breathing tube can also protrude on the side facing the patient.

An alternative embodiment in which the ambient air is inhaled and exhaled into the ambient air comprises the fact that the breathing tube possesses a mouthpiece to which a tube portion is connected. A filter material with a sock shape or a sack shape or shaped like a concertina is positioned at the tube portion which filter material is permeable for ultrasonic waves and largely impermeable to germs and contaminants. This filter material can consist in all embodiments of a suitable hydrophobic filter material, for example, of glass fibres, polypropylene fibres or polycarbonate fibres.

The breathing tube together with its different parts, including its mouthpiece, can be formed from one piece. For both technical and economic reasons, the breathing tube can, however, possibly also be produced from several materials. Here, two or more materials can be used. In the area outside the graduated channels, that is at and opposite to the patient, materials are used which possess rigidity, shape retention, accuracy to size and impermeability to gas and which simultaneously allow favourably priced manufacture. Materials which can be used for this are, for example, polyethylene, polypropylene or polycarbonate which is particularly easy to process and which possesses favourable properties for use and is capable of recycling.

In the central area, materials are used which are permeable for ultrasound, but impermeable to germs and contaminants, for example the previously named hydrophobic filter material made from glass fibres, polypropylene fibres or polycarbonate fibres.

One very simple embodiment can comprise the fact that the breathing tube essentially consists only of filter material.

The material permeable for ultrasonic waves can, in accordance with a further embodiment, be impermeable to gas. In this case, a measurement of certain pulmonary function parameters can be performed by a corresponding inlet of test gases. Thus, for example, the residual volume can be determined here.

Figure 4:
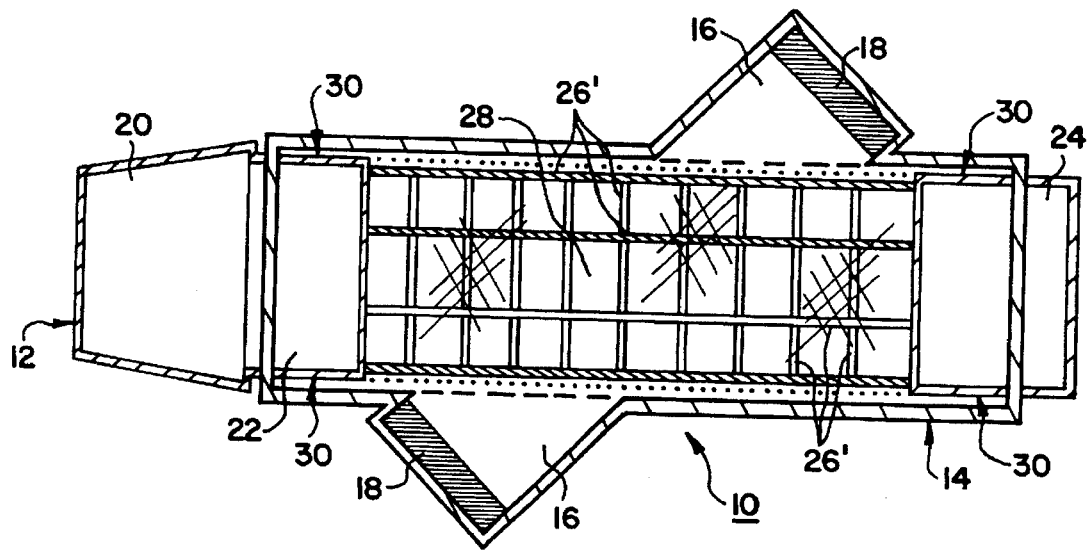
Figure 5:
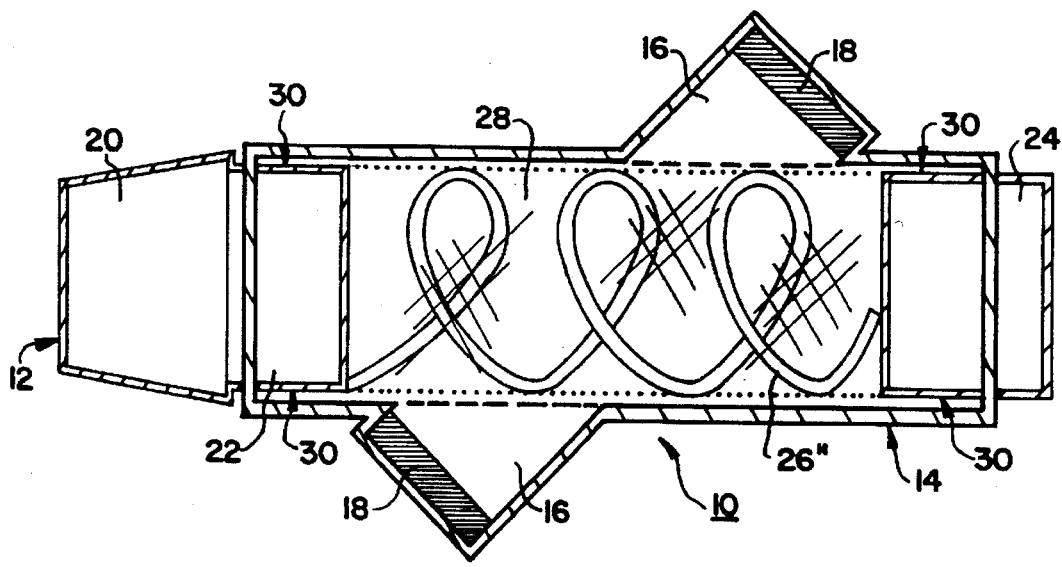

Further details and advantages are produced from the description of the following figures of preferred embodiments. Here FIG. 1 shows a schematic drawing in side-view of a first embodiment of the ultrasonic spirometer in accordance with the present invention, FIG. 2 a schematic drawing in side-view of a second embodiment of an ultrasonic spirometer in accordance with the present invention, FIG. 3 a schematic drawing in side-view of a third embodiment of an ultrasonic spirometer in accordance with the present invention, FIG. 4 a schematic similar to FIG. 1 but showing one alternative, and FIG. 5 a schematic similar to FIG. 1 but showing another alternative.

The ultrasonic spirometer 10 shown in FIG. 1 consists of a graduated tube 14 already sufficiently known as such and a graduated channel 16 positioned diagonally to this at whose ends the ultrasonic transducers 18 are positioned.

In the graduated tube the breathing tube 12 is inserted in a manner also already known. The replaceable breathing tube 12 is divided into three sections. The front section close to the patient consists of a front tube portion 22 to which a mouthpiece 20 has been shaped in one piece. The rear section consists of a rear tube portion 24 which protrudes out of the graduated tube 14 and to which gas hose 25 can be flanged in a gas-impermeable manner in a manner not shown in detail here. In the intermediate section spacers in the shape of struts 26 in parallel to each other are positioned which connect the front tube portion 22 to the rear tube portion 24. The front tube portion 22 with the mouthpiece 20, the rear tube portion 24 and the struts 26 consist of polyethylene or polypropylene. The spacers designed here as struts can, in an alternative embodiment, also be formed as a mesh 26' (FIG. 4) or a spiral 26" (FIG. 5) to improve the stability. The section between the from tube portion 22 and the rear tube portion 24 is sealed with a filter material which is permeable for ultrasonic waves, but largely impermeable to bacteria or other contaminants. The distance between the front tube portion 22 and the rear tube portion 24 possesses such a dimension that the graduated channel 16 lies in the area of the intermediate section sealed with filter material. The filter material 28 is laid around the struts 26 in the shape of tubes and connected fast, i.e. glued or welded, to the joint abutments of the front tube portion 22 or the rear tube portion 24. The filter material 28 can consist of a suitable hydrophobic filter material, for example of glass fibre or polypropylene fibre.

Between the front tube portion 22 and/or the rear tube portion 24 and the graduated tube 14 packing washers are positioned over the whole circumference. The packing washers press onto the inside walls of the graduated tube 14 during the introduction of the replaceable breathing tube 12 into the graduated tube 14. In this way, the breathing tube 12 can be inserted into the graduated tube 14 in a manner impermeable to gas over the environment.

To ensure a better fit of the replaceable breathing tube 12 in the graduated tube 15, a recess groove can be stamped into the inside wall of the graduated tube 14 in place of the packing washers 30 covering the whole circumference. In place of the packing washers 30 already mentioned, suitable O rings can also be used for sealing. The use of gaskets 30 is altogether necessary particularly when the breathing tube is jointed to a gas-supplying hose or valve on the side mined away from the patient and a gas-impermeable feed of the respiratory gas without any leak or any penetration of foreign gas from the environment needs to be obtained.

Figure 2:
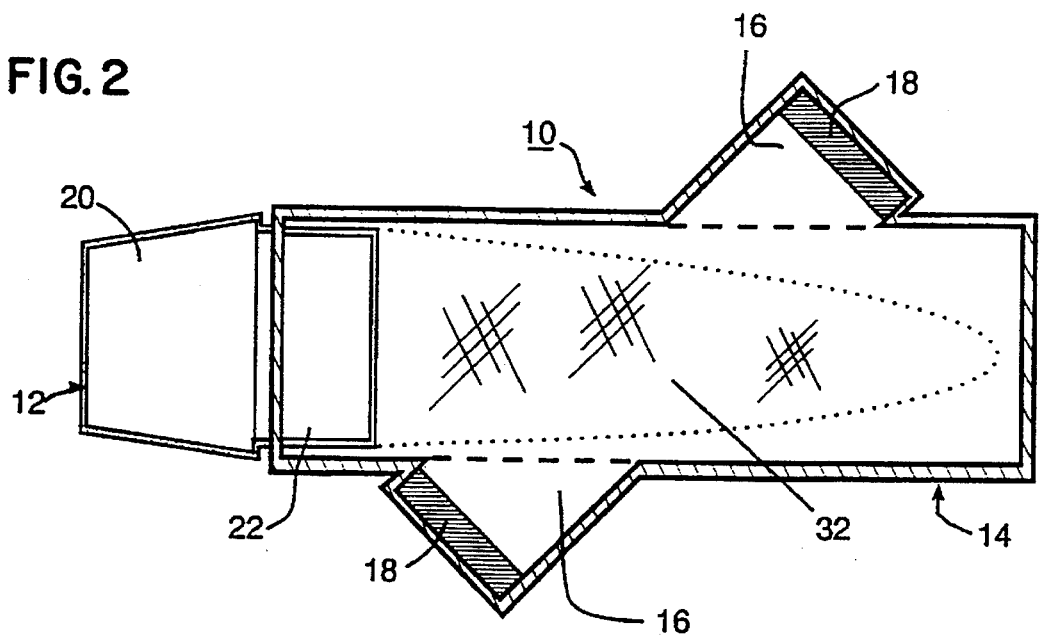

A further embodiment is produced from the representation in accordance with FIG. 2. Identical parts are designated with identical reference symbols in this embodiment. Here, too, an ultrasonic spirometer is presented which possesses a graduated tube 14 known per se with a graduated channel 16 and ultrasonic transducers 18 as the transmitter/receiver cell pair. In the graduated tube 14, a breathing tube 12 is inserted which is, however, here modified over the first embodiment. The replaceable breathing tube 12 represented here should be used exclusively for simple spirometric purposes, that means that no respiratory gas should be supplied. In this case, the breathing tube can essentially comprise two parts. The part close to the patient is designed as previously described and consists of a front tube portion 22 with a shaped mouthpiece 20. In contrast to the version described previously, there is no middle or rear portion of the breathing tube. In their places, a filter material 32 with a sock shape or a sack shape or in the form of a concertina is connected to the front tube portion 22. In the design of the filter material the largest possible surface should be selected as this will lead to improved bacterial retention. The part 32 formed from the filter material can maintain its shape thanks to its own rigidity or to the additional application of a suitable, e.g. basket-shaped, forming part to the replaceable breathing tube. The forming part can consist of the same material as the tube piece. The filter material is applied to the front tube portion 22 in such a way that no openings are created through which bacteria can penetrate. This can be achieved by gluing or welding.

Apart from the materials listed previously, for this application cardboard, paper or stable, organic material can be used to manufacture the mouthpiece or the front tube portion. With this embodiment where the respiratory air is inhaled from the environment and exhaled again into the environment, an insertion of the breathing tube 12 into the graduated tube 14 in an gas-impermeable manner is not necessary.

Figure 3:
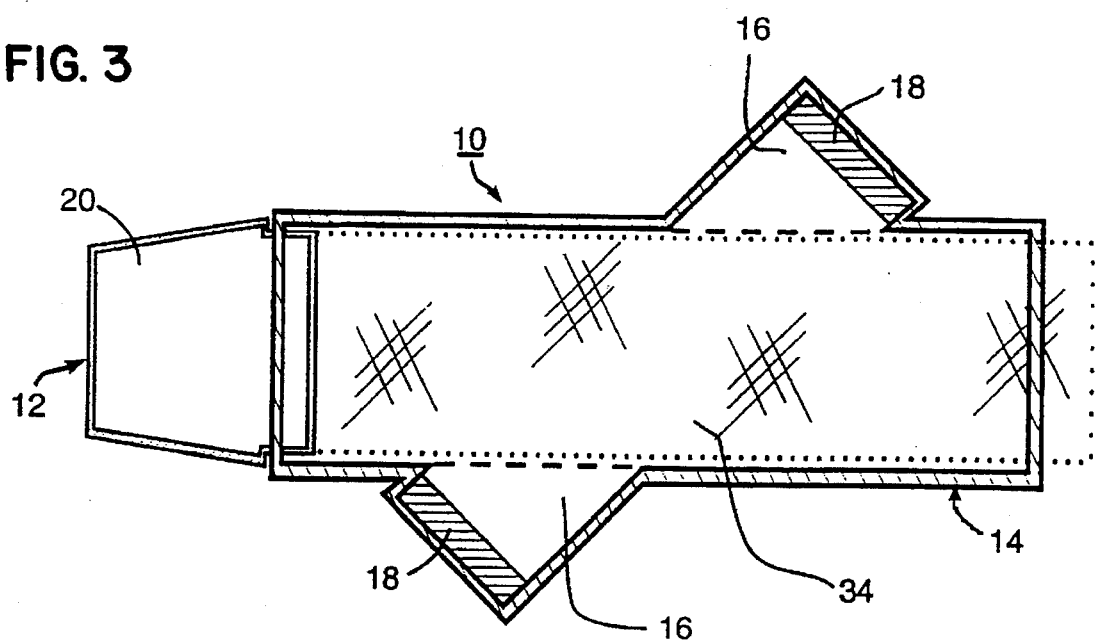

FIG. 3 shows an embodiment which is similar to that in accordance with FIG. 2. Here, however, in place of the shaped part 32 a tube-shaped filter material 34 is connected directly to the mouthpiece 20. This tube-shaped filter material 34 protrudes over the graduated tube 14 at the rear. In this way, it is prevented that germs and contaminants settle in the end section of the graduated tube. The mouthpiece 20 can be inserted into the graduated tube using an attachment in a manner not shown in any detail.

I claim:

1. An ultrasonic spirometer comprising:
   a graduated tube extending along a graduated tube axis,
   a transmitter/receiver cell pair positioned in a graduated portion of said graduated tube disposed at an angle to the graduated tube axis,
   an easily replaceable breathing tube insertable into the graduated tube, the breathing tube including one material which is permeable for ultrasonic waves but substantially impermeable to germs and contaminants,
   the material being positioned in an area in which the graduated portion of said graduated tube intersects the graduated tube and over an entire circumference of the breathing tube.

2. An ultrasonic spirometer according to claim 1, wherein the breathing tube comprises a mouthpiece and a front tube portion connected to said mouthpiece, a rear tube portion and a middle tube portion positioned between the front tube portion and the rear tube portion, the material being positioned over the entire circumference in said middle tube portion.

3. An ultrasonic spirometer according to claim 2, and further comprising a support element extending between the front tube portion and the rear tube portion on which the material lies.

4. An ultrasonic spirometer according to claim 2, and further comprising a support element connected to the front tube portion on which the material lies.

5. An ultrasonic spirometer according to claim 3, wherein the support element consists of parallel struts.

6. An ultrasonic spirometer according to claim 3, wherein the support element consists of a grid-like mesh.

7. An ultrasonic spirometer according to claim 3, wherein the support element consists of a spiral covering the circumference in said middle tube portion.

8. An ultrasonic spirometer according to claim 2, wherein the front tube portion and the rear tube portion of the breathing tube are sealed in a gas-impermeable manner together with the graduated tube.

9. An ultrasonic spirometer according to claim 1, wherein the breathing tube includes a mouthpiece and a tube portion connected to said mouthpiece, and said material has a sock shape and is connected to the breathing tube.

10. An ultrasonic spirometer according to claim 1, wherein the material consists of a hydrophobic filter material made from any of glass fibres, polypropylene fibres and polycarbonate fibres.

11. An ultrasonic spirometer according to claim 1, wherein a portion of the breathing tube consists of said material.

12. An ultrasonic spirometer according to claim 1, wherein the breathing tube protrudes past an end of the graduated tube.

13. An ultrasonic spirometer according to claim 1, wherein the material is additionally impermeable to gas.

14. An ultrasonic spirometer according to claim 1, wherein a rear portion of the breathing tube is formed so that a gas hose can be connected to it in a gas impermeable manner.

15. An ultrasonic spirometer according to claim 1, and further comprising a mouthpiece defined by a front portion of the breathing tube.

* * * * *